(12) United States Patent
Arcos Jiménez et al.

(10) Patent No.: US 6,200,784 B1
(45) Date of Patent: Mar. 13, 2001

(54) PROCESS FOR THE SELECTIVE PREPARATION OF DERIVATIVES OF MONOSACCHARIDES AND POLYOLS WHICH ARE PARTIALLY ACYLATED

(75) Inventors: José Antonio Arcos Jiménez; Cristina Otero Hernández, both of Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 09/269,997

(22) PCT Filed: Oct. 1, 1997

(86) PCT No.: PCT/ES97/00240

§ 371 Date: Dec. 9, 1999

§ 102(e) Date: Dec. 9, 1999

(87) PCT Pub. No.: WO98/15640

PCT Pub. Date: Apr. 16, 1998

(30) Foreign Application Priority Data

Oct. 4, 1996 (ES) .................................................. 9602091

(51) Int. Cl.$^7$ .............................. C12P 19/02; C12N 9/20
(52) U.S. Cl. ............................................. 435/105; 435/198
(58) Field of Search ....................................... 435/105, 198

(56) References Cited

U.S. PATENT DOCUMENTS 5,508,182 * 4/1996 Schneider et al. .

FOREIGN PATENT DOCUMENTS

| 0274798 | 7/1988 | (EP) . |
| 0334498 | 9/1989 | (EP) . |
| 0481147 | 4/1992 | (EP) . |
| 0506159 | 9/1992 | (EP) . |
| 61038062 | 8/1987 | (JP) . |
| 61131362 | 12/1987 | (JP) . |

* cited by examiner

*Primary Examiner*—Francisco Prats
*Assistant Examiner*—Susan D. Coe
(74) *Attorney, Agent, or Firm*—Klauber & Jackson

(57) ABSTRACT

The process relates to the very selective enzymatic production of monosaccharides and polyols which are mono and/or bisubstituted with fatty acids. The process is based on the simple mixing of polyol or monosaccharide with the fatty acid, the addition of solvent, and the use of lipases in order to regioselectively obtain them without catalysts or toxic agents. The process requires continuous removal of water produced during the process. The invention applies to the sectors such as food, pharmaceutics, cosmetics and chemistry. The products obtained are excellent non ionic surfactant agents, which are biocompatible and biodegradable and are used as additives due to their emulgent, unctuous, thickening and hydrating characteristic.

13 Claims, No Drawings

PROCESS FOR THE SELECTIVE PREPARATION OF DERIVATIVES OF MONOSACCHARIDES AND POLYOLS WHICH ARE PARTIALLY ACYLATED

TECHNICAL FIELD OF THE INVENTION

The invention belongs to the alimentary, pharmaceutical, cosmetic and chemical sectors. The products obtained are excellent biodegradable and biocompatible non-ionic tensioactive agents which are used as additives for their emulsifying, oily, thickening and moisturising properties.

DESCRIPTION OF PRIOR ART

The employment of enzymes in organic media is an attractive alternative to classical organic synthesis. The main drawbacks of conventional chemical techniques are their high energy consumption (high temperatures and pressures), the low selectivity of the processes and/or the employment of inorganic catalysts which produce coloured impurities of variable toxicity. In contrast, enzymatic catalysts can achieve selective synthesis of a given product under less extreme pressures and temperatures and are less environmentally toxic.

Lipases are the hydrolytic enzymes most effective at catalytic processes involving long chain fatty acids. These form covalent bonds with alcohols in media with a low degree of hydration. Because of their versatility and wide availability these make very valuable industrial biocatalysts. Besides, lipases are biodegradable. When several hydroxyl groups are present in the same molecule, because of their extreme selectivity lipases can replace long synthetic pathways (with phases of protection/exposure) with one enzymatic step. This increases yields and reduces the cost of the process itself and also that associated with treatment of the waste products [Biocatalysts for industry (1991) Plenum Press, N.Y. Ed. J. Dordick] compared to alternative chemical processes. Moreover, the chemo- and enantioselectivity of lipases can give rise to highly competitive synthetic processes.

More than 80% of the world market of tensioactive agents are molecules formed by condensation between polyols or monosaccharides and long chain fatty acids (glycerides, spans, tweens etc.). Esterified sorbitan derivatives with long chain fatty acids are biocompatible glycolipid surfactants commonly used in a variety of industries. The commercial name for esterified sorbitan derivatives is Spans. These are highly lipophilic and are precursors of Tweens. At present, Tweens™ and Spans™ are prepared industrially by non-enzymatic procedures at 180–150° C. Gluco and glycolipidic surfactants are additives used in cosmetic and pharmaceutical products for their different properties (moisturizing and lubricative capacities etc.). The employment of many of these emulsifiers, which are themselves biocompatible, for certain applications (e.g. in the alimentary sector) is often problematic. These problems are related with the conventional chemical method used in their preparation. The presence of certain synthetic agents in the chemical processes used to manufacture or purify the additive constitute one of the main drawbacks of the preparation methods used. Selective obtainment of emulsifiers by enzymes can solve this problem. European and American legislation consider substances produced or modified by enzymes as natural products.

The enzymatic production of glucolipidic tensioagents derived from monosaccharides and polyols has been studied in the literature although only low yields were obtained [Khaled, N., Montet, D. Pina, M. and Graille, J. Biotech. Let., 13, 167–172 (1991) and Schlotterbeck, A. Lang, S., Wray, V. and Wagner, F. Biotechnol. Lett. 15, 61–64 (1993)] and/or these require preliminary non-enzymatic steps [Fregapane, G., Sarney, D. B. and Vulfson, E. N. Enz. Microb. Technol.13, 796–800 (1991) and Bjorklong, F., Godtfredsen, S. E. and Kirk, O. J. Am. Soc. chem. Commun. 934–935 (1989)]. One enzymatic method based on an aqueous mixture of reagents at 20–60° C. [DE-B-3430944 (SEINO)] and the later improved version of the process using high pressure water evaporation [JP-A-62195-292] have been disclosed. In both cases the yields obtained are relatively low due to displacement of the thermodynamic equilibrium of the aqueous process towards hydrolysis. The sugars recommended in these patents are glucose, saccharose, raffinose, dextrin, mannan, cellulose, sorbitol and xylitol. Yields have been increased using almost anhydrous organic media and increasing the solubility of the starting sugar in the medium by previous chemical modification. This was also the aim of a number of international patents. A further esterification process, JP-A-63-112993, published on the of May 18, 1988 includes a preliminary step that consists of acetylating the sugar, whereas according to EP-A-0334498 the glucoside is alkylated before carrying out the enzymatic acylation. The processes described in the aforecited prior art literature all include a previous non-enzymatic step to decrease the polarity of the substrate followed by enzymatic processes with high yields. However, the tensioactive molecules obtained are more complex than those obtained with the previous methods.

EP-A-0506159 and EP-A-0274798 disclose processes for esterification of carboxylic acids with alcohols in the presence of lipases. Due to that the alcohols are immediately miscible with the acids, or made immediately miscible by dissolving them in a suitable solvent, the alcohols immediately contact the lipase and the carboxylic acids, whereby not only primary but also secondary hydoxyls of the alcohols are esterified whereby rather heterogeneous reaction products are obtained. The disadvantage of said processes is that no selective esterification is possible.

BRIEF DESCRIPTION OF THE INVENTION

This invention as claimed consists of an enzymatic procedure of selective synthesis of partially acylated polyol and monosaccharide esters with fatty acids in almost anhydrous media. Quantitative or almost quantitative yields are obtained in only one step.

DETAILED DESCRIPTION OF THE INVENTION

The invention refers to the highly selective enzymatic production of monosaccharides and polyols being mono and/or disubstituted with fatty acids. The procedure is based on a simple mixture of polyol or monosaccharide with the fatty acid, the addition of solvent and the use of lipases that permit the highly selective obtainment of these products without catalysts or toxic agents. The water produced during the process must be continually removed throughout the process.

The tensioactive agents synthesized present a higher biodegradability than ethoxylated alkyl phenols commonly used in washing powders etc.

Moreover, these enzymatic reactions permit the recovery and reassessment of the waste products. Lipases can act with pure fatty acids and also with mixtures of these derived from natural oils and fats (olive, coconut or palm oil etc.) The European Union produces large surpluses of oils and fats. Minimization of the waste products and the recovery of by-products (oils and fats) and their industrial reassessment and recycling is one of the priority objectives in Europe and elsewhere.

The chemical procedures currently used for the industrial preparation of these products involve high energy consumption and the corresponding installations for conditions of high pressure and temperature. Because of the low selectivity of these chemical procedures [U.S. Pat. No. 2,759,922], unlike enzymatic processes these chemical procedures can not obtain products with a specific and constant structure. Previously patented enzymatic procedures [DE-B-3439944 (SEINO) and JP-A-62195292] which use aqueous medium, achieve very low yields, limiting their industrial use. The present enzymatic process can achieve almost quantitative yields by direct esterification of the polyol and/or monosaccharide in an almost anhydrous organic medium. Our invention can directly use the polyol or sugar without the prior chemical modification described in JP-A-63-112993 and EP-A-0334498 which obtain different final products than those obtained here. In both these procedures the previous non-enzymatic step and also the possible use of solvents with a high boiling point make the patented processes more expensive than the present procedure. The present method preferentially uses cheaper solvents of easy elimination and low toxicity.

The invention is applicable to linear polyols such as sorbitol. Also, monosaccharides such as glucose, fructose, mannose etc. can be selectively transformed. The reaction with galactose is less selective and results in a greater mixture of mono and diesters.

With the patented procedure, different fatty acids of variable chain length, preferably from C8 to C22 can be used. The acid chain can be saturated or unsaturated, linear or branched (i.e. octanoic acid, hexadecanoic acid, oleic acid etc.). Also, a mixture of fatty acids can be used (i.e. industrial acids from coconut, soya, corn, cotton seeds, etc.). Direct use of ethylic esters of fatty acids is much less effective in these processes.

High temperatures are not required although they can be used in some cases. Milder temperatures (0–60° C.) are generally preferred.

The process can be catalyzed by lipolytic enzymes of yeast or animal, vegetable, bacterial or fungal origin. This can be in a native form, immobilized in an inert support and/or modified chemically or can be obtained by genetic engineering. Thus, high yields have been obtained with immobilized lipases of *Candida antartica* (Novozim 435) and *Mucor miehie* (Lipazyme IM) prepared by Novo Industria A/S, with Novozim 435 proving very effective.

Selective esterification of primary hydroxyls is produced and the secondary hydroxyls remain unaltered.

The process can be carried out in different solvents or relatively polar organic media in order to, at least partially, solubilize the polyol (or the sugar), preferentially ones with a low boiling point to facilitate their elimination.

The solvent and the reagents should have a low water content, preferentially below 5% w/w and if possible in the range of 0.01 to 1% w/w.

The fatty acid content should preferredly be above 100 mM and have a molar excess of 1.5 times that of the sugar.

The process should be carried out in a continuously agitated tank. The amount of enzyme required depends on the specific activity of the enzyme preparation used.

The invention will be specifically described hereinafter by the following examples:

EXAMPLE 1

Synthesis of Glucose 6-Monolaurate

EXAMPLE A 2 ml of acetone were added to the reactor which contained 100 mg of Novozim 435, 60 mg of glucose and 200 mg of lauric acid. The reaction was carried out under mild continual agitation at 40° C. and water was continually removed from the reaction medium. 121 mg of glucose 6-monolaurate were obtained after 3 days of reaction corresponding to a yield of 99%.

EXAMPLE B 8 g of Novozim 435, 5 g of glucose and 16.7 g of lauric acid were added to 160 ml of acetone. After 5 days of mild agitation at 40° C. with constant removal of water from the reaction mixture, 9.6 g of glucose 6-monolaurate (98% yield) were obtained.

EXAMPLE C 80 g of Novozim 435, 50 g of glucose and 167 g of lauric acid were added to 1.6 l of acetone. After 6 days of mild agitation at 40° C. and with continuous removal of water from the reaction medium 90 g of glucose 6-mono-laurate were obtained (90% yield).

EXAMPLE 2

Reaction Between Sorbitol and the Fatty Acids Derived From Hydrolysis of Olive Oil 60 mg of sorbitol, 480 mg of a mixture of fatty acids and 100 mg of Novozim 435 were added to 2 ml of acetone. The reaction was carried out under continuous mild agitation and water was continually removed from the medium that was maintained at 40° C. for 6 h and later at 10° C. 234 mg of 1,6 sorbitol diester and 8 mg of monoester corresponding to yields of 94% and 2% respectively were obtained.

EXAMPLE 3

Reaction Between Mannose and Lauric Acid

This reaction used 60 mg of mannose and 200 mg of lauric acid in 2 ml of acetone in the presence of 100 mg of Novozim 435, the reaction mixture was maintained at 60° C. and under continuous mild agitation and water was continually removed from the reaction mixture. 107 mg of monoester and 18 mg of diester were obtained after 15 hours. The yields were 90% and 10%, respectively.

What is claimed is:

1. A process for selective preparation of partially acylated monosaccharide and linear polyol derivatives which are esterified only in respect of their primary hydroxyls, the process comprising the steps of preparing a reaction mixture of a solid linear polyol or a monosaccharide with the exception of galactose, a fatty acid or a mixture of fatty acids, and a solvent, and contacting the reaction mixture with a lipase, and continuously removing water formed during the process wherein the process is carried out at a reaction temperature between 0° and 60° C.;

the water in the reaction mixture is maintained between 0.001 and 5% wt/wt;

the fatty acid or mixture of fatty acids, is added in a concentration higher than 100 mM and in a molar excess of at least 1.5 fold, in respect of the polyol or the monosaccharide, the process is carried out such that selective esterification of primary hydroxyls of the polyol or monosaccharide is achieved without alteration of secondary hydroxyls thereof;

the solvent is acetone.

2. A process according to claim 1, wherein the lipase is selected from the group of immobilized lipases of *Candida antartica* and *Mucor miehie*.

3. A process according to claim 1, wherein the mixture of fatty acids comprises $C_8$–$C_{22}$ fatty acids having a linear or branched, saturated or insaturated chain.

4. A process according to claim 1, wherein the fatty acid is lauric acid.

5. A process according to claim 1, wherein the fatty acid is selected from the group consisting of octanoic acid, hexadecanoic acid and oleic acid.

6. A process according to claim 1, wherein the fatty acid is selected from the group consisting of industrial acids from coconut, soya and cotton seeds.

7. A process according to claim 3, wherein the mixture comprises at least one of octanoic acid, hexadecanoic acid and oleic acid.

8. A process according to claim 1, wherein the mixture comprises at least one industrial acid from the group consisting of coconut, soya and cotton seeds.

9. A process according to claim 1, wherein the reaction temperature is 0–40° C.

10. A process according to claim 9, wherein the reaction temperature is 40° C.

11. A process according to claim 1, wherein the monosaccharide is selected from the group consisting of glucose, mannose and fructose.

12. A process according to claim 1, wherein the linear polyol is sorbitol.

13. A process according to claim 1, wherein the polyol is sorbitol and the reaction mixture is maintained at a temperature of 40° C. for 6 h and thereafter maintained at 10° C. until esterification has been completed.

* * * * *